United States Patent [19]

Maurer et al.

[11] Patent Number: 4,771,040
[45] Date of Patent: Sep. 13, 1988

[54] 6-OXO-PYRIMIDINYL(THIONO)-PHOSPHATE PESTICIDES

[75] Inventors: Fritz Maurer, Wuppertal; Bernhard Homeyer; Paul Reinecke, both of Leverkusen, all of Fed. Rep. of Germany

[73] Assignee: Bayer Aktiengesellschaft, Leverkusen, Fed. Rep. of Germany

[21] Appl. No.: 13,081

[22] Filed: Feb. 10, 1987

[30] Foreign Application Priority Data

Feb. 18, 1986 [DE] Fed. Rep. of Germany ....... 3605002

[51] Int. Cl.$^4$ .......................... A01N 57/16; C07F 9/65
[52] U.S. Cl. ......................................... 514/86; 544/243
[58] Field of Search .......................... 544/243; 514/86

[56] References Cited

U.S. PATENT DOCUMENTS

| 4,152,426 | 5/1979 | Maurer et al. | 514/86 |
| 4,575,499 | 3/1986 | Reinfschneider | 514/86 |

FOREIGN PATENT DOCUMENTS

| 2722402 | 11/1978 | Fed. Rep. of Germany . | |
| 3317824 | 11/1984 | Fed. Rep. of Germany | 544/243 |
| 3445465 | 6/1986 | Fed. Rep. of Germany | 514/86 |
| 3527861 | 2/1987 | Fed. Rep. of Germany . | |
| 1369062 | 8/1963 | France . | |
| 2356663 | 1/1978 | France . | |

Primary Examiner—Donald G. Daus
Assistant Examiner—Diana G. Rivers
Attorney, Agent, or Firm—Sprung Horn Kramer & Woods

[57] ABSTRACT

Insecticidally and fungicidally active novel 6-oxopyrimidinyl (thiono)-phosphate of the formula

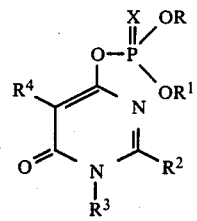

in which
X represents oxygen or sulphur,
R represents alkyl,
$R^1$ represents fluoroalkyl,
$R^2$ represents hydrogen, optionally substituted alkyl, or alkoxy, alkylthio, dialkylamino or aryl,
$R^3$ represents alky or aryl and
$R^4$ represents hydrogen, halogen or alkyl.

11 Claims, No Drawings

6-OXO-PYRIMIDINYL(THIONO)-PHOSPHATE PESTICIDES

The present invention relates to new 6-oxo-pyrimidinyl (thiono)-phosphates, processes for their preparation, and their use as plant-protecting agents, preferably as insecticides and fungicides.

It is already known that O,O-dialkyl 6-oxo-pyrimidinyl phosphates, such as, for example, O,O-diethyl O-(1,6-dihydro-1-methyl-2-i-propyl-6-oxo-pyrimidin-4-yl) thionophosphate, O-ethyl O-n-propyl O-(1,6-dihydro-1-methyl-2-i-propyl-6-oxo-pyrimidin-4-yl) thionophosphate and O,O-diethyl O-(1,2-diethyl-1,6-dihydro-6-oxo-pyrimidin-4-yl) thionophosphate, have insecticidal properties (cf. DE-OS (German Published Specification) No. 2,630,054 and the corresponding U.S. Pat. No. 4,152,426).

The new 6-oxo-pyrimidinyl (thiono)-phosphates of the formula (I),

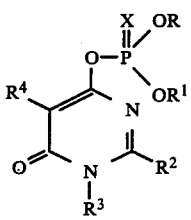

in which
X represents oxygen or sulphur,
R represents alkyl,
$R^1$ represents fluoroalkyl,
$R^2$ represents hydrogen, optionally substituted alkyl, or alkoxy, alkylthio, dialkylamino or aryl,
$R^3$ represents alkyl or aryl and
$R^4$ represents hydrogen, halogen or alkyl, have now been found.

It has furthermore been found that the 6-oxo-pyrimidinyl (thiono)-phosphates of the formula (I) are obtained when (a) halides of the formula (II)

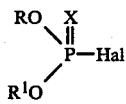

in which
X, R and $R^1$ have the abovementioned meanings and
Hal represents halogen, preferably chlorine, are reacted with 1,6-dihydro-4-hydroxy-6-oxo-pyrimidines of the formula (III)

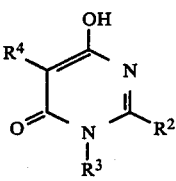

in which
$R^2$, $R^3$ and $R^4$ have the abovementioned meanings, if appropriate in the presence of an acid acceptor and if appropriate in the presence of a solvent; or when (b) in the case where $R^3$ represents alkyl, O-(6-hydroxy-pyrimidin-4-yl) (thiono)-phosphates of the formula (IV)

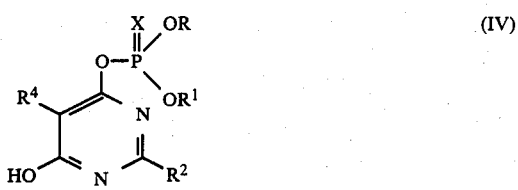

in which
X, R, $R^1$, $R^2$ and $R^4$ have the abovementioned meaning,
(α) are reacted with alkylhalides of the formula (V)

in which
$R^3$ represents alkyl and
$Hal^1$ represents halogen (preferably chlorine, bromine or iodine), or
(β) are reacted with dialkyl sulphates of the formula (VI)

in which
$R^3$ represents alkyl, if appropriate in the presence of an acid acceptor and if appropriate in the presence of a solvent.

Surprisingly, the 6-oxo-pyrimidinyl (thiono)-phosphates, of the formula (I), according to the invention are distinguished, in an outstanding fashion, by a particularly high and long-term activity as plant-protecting agents, particularly insecticides and acaricides, particularly preferably as insecticides and fungicides. They also display, in particular, a very good activity in the case of treatment of the soil.

Optionally substituted alkyl $R^2$ and the alkyl radicals R, $R^3$ and $R^4$, and also the alkyl parts of the alkoxy, alkylthio and dialkylamino radicals $R^2$, can be branched or unbranched and preferably contain 1 to 8, particularly 1 to 6 and particularly preferably 1 to 4, carbon atoms in each case. Examples which may be mentioned are: methyl, ethyl, n-propyl, isopropyl, n-butyl, isobutyl, sec.-butyl, tert.-butyl, methoxy, ethoxy, n-propoxy, isopropoxy, n-butoxy, sec.-butoxy, isobutoxy, tert.-butoxy, methylthio, ethylthio, n-propylthio, iso-propylthio, n-butylthio, iso-butylthio, sec.-butylthio, tert.-butylthio, dimethylamino, diethylamino, di-n-propylamino, di-iso-propylamino, di-n-butylamino, di-iso-butylamino, di-sec.-butylamino or di-tert.-butylamino.

Alkyl R preferably denotes methyl, ethyl or n- and i-butyl. Alkyl $R^2$ preferably denotes methyl, ethyl or n- and i-propyl. Alkyl $R^3$ preferably represents methyl or ethyl. Preferred alkyl $R^4$ is methyl or ethyl.

The aryl radical $R^2$ preferably contains 6 and 10 carbon atoms in the aryl part. Examples which may be mentioned are: naphthyl or phenyl, particularly phenyl.

The fluoroalkyl radical $R^1$ can be branched or unbranched and preferably contains 1 to 8, particularly 1 to 6 and particularly preferably 1 to 4, carbon atoms and 1 to 8, preferably 1 to 6 and particularly preferably 1 to 4, fluorine atoms. Examples which may be mentioned are: trifluoromethyl, 2,2,2-trifluoroethyl, difluoroethyl, 3,3,3-trifluoro-1-propyl, 2,2,3,3-tetrafluoro-1-propyl, 1,1,1,3,3,3-hexafluoro-2-propyl, 2-trifluoromethyl-2-propyl and 2,2,3,4,4,4-hexafluoro-1-butyl. 2,2,2-Trifluoroethyl and 2,2,3,3-tetrafluoro-1-propyl are particularly preferred.

Halogen denotes (where not otherwise stated) fluorine, chlorine, bromine or iodine, preferably fluorine, chlorine and bromine, particularly chlorine.

In the definition of $R^2$, optionally substituted alkyl can carry one or more, preferably 1 to 3, particularly 1 or 2, identical or different substituents. Examples which may be mentioned are: halogens, such as fluorine, chlorine and bromine, nitro, cyano, and also alkoxy and alkylthio having preferably 1 to 4, particularly 1 and 2, carbon atoms. The alkyl radical $R^2$ is particularly preferably unsubstituted.

In the general formulae, X preferably denotes sulphur.

In the general formulae, $R^4$ preferably denotes hydrogen.

The invention preferably relates to compounds of the formula (I) in which

X represents oxygen or sulphur (preferably sulphur),
R represents alkyl having 1 to 6 carbon atoms,
$R^1$ represents fluoroalkyl having 1 to 6 carbon atoms and 1 to 6 fluorine atoms,
$R^2$ represents hydrogen, alkyl, having 1 to 6 carbon atoms, which is optionally substituted by fluorine, chlorine, bromine, nitro, cyano, $C_1$-$C_4$-alkoxy or $C_1$-$C_4$-alkylthio, alkoxy, alkylthio or dialkylamino having in each case 1 to 6 carbon atoms per alkyl part, or phenyl,
$R^3$ represents alkyl having 1 to 6 carbon atoms, or phenyl and
$R^4$ represents hydrogen, fluorine, chlorine or bromine or alkyl having 1 to 6 carbon atoms.

Particularly preferred compounds of the formula (I) are those in which

X represents oxygen or sulphur (preferably sulphur),
R represents alkyl having 1 to 4 carbon atoms (preferably methyl, ethyl, n-propyl and i-propyl),
$R^1$ represents fluoroalkyl having 1 to 4 carbon atoms and 1 to 6 fluorine atoms (preferably trifluoromethyl, 2,2,2-trifluoroethyl, 2,2,3,3-tetrafluoropropyl and 1,1,1,3,3,3-hexafluoro-2-propyl, particularly 2,2,2-trifluoroethyl or 2,2,3,3,-tetrafluoropropyl),
$R^2$ represents hydrogen, alkyl, having 1 to 4 carbon atoms, which is optionally substituted by fluorine, chlorine, methoxy, ethoxy, methylthio or ethylthio, alkoxy having 1 to 4 carbon atoms, alkylthio having 1 to 4 carbon atoms, dialkylamino having 1 to 4 carbon atoms per alkyl radical, or phenyl (preferably methyl, ethyl, n- and i-propyl, methylthio or methylthiomethyl,
$R^3$ represents alkyl having 1 to 4 carbon atoms, or phenyl (preferably methyl or ethyl) and
$R^4$ represents hydrogen, fluorine, chlorine or bromine, or alkyl having 1 to 4 carbon atoms (preferably hydrogen, methyl or ethyl, particularly hydrogen).

Very particularly preferred compounds of the formula (I) are those in which

X represents sulphur,
R represents ethyl,
$R^1$ represents $CH_2CF_3$ or $CH_2CF_2CHF_2$,
$R^2$ represents ethyl, i-propyl or methylthio,
$R^3$ represents methyl or ethyl and
$R^4$ represents hydrogen.

If, for example, O-ethyl O-(2,2,2-trifluoroethyl) thionophosphate chloride and 1,6-dihydro-4-hydroxy-1-methyl-6-oxo-pyrimidine are used as starting materials, then the corresponding reaction can be represented by the following equation:

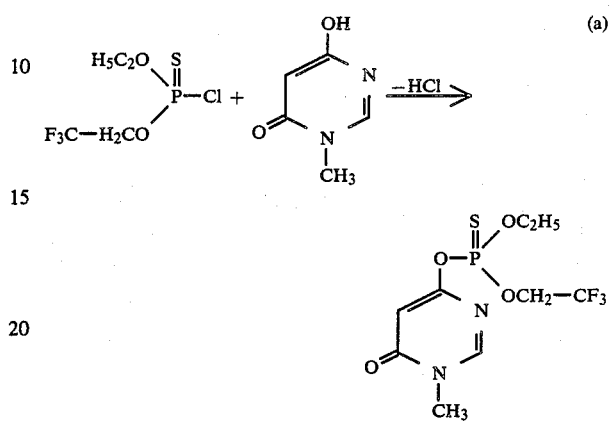
(a)

If, for example, O-ethyl O-(2,2,2-trifluoroethyl) O-(5-ethyl-6-hydroxy-2-i-propyl-pyrimidin-4-yl) thionophosphate and methyl iodide are used as starting materials, then the corresponding reaction can be represented by the following equation:

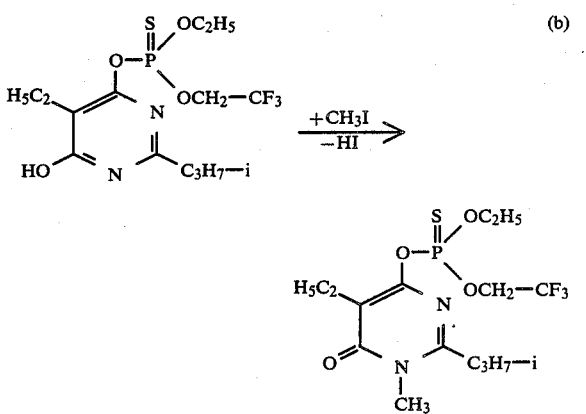
(b)

The halides to be employed as starting materials are defined by the formula (II). In this formula, X, R and $R^1$ represent those radicals which are stated in the definition in formula (I). In this formula, Hal represents halogen, particularly chlorine or bromine, particularly preferably chlorine.

The compounds of the formula (II) are the subject of U.S. Application Ser. No. 886,283, filed July 15, 1986, now pending. They can be prepared in a simple manner by known methods, by reacting dihalides of the formula (VII),

(VII)

in which R, X and Hal have the abovementioned meanings, with alcohols of the formula (VIII)

(VIII)

in which R¹ has the abovementioned meaning, in the presence of acid acceptors, such as, for example, collidine, N,N-dimethylaniline, dimethylbenzylamine, pyridine or triethylamine, and in the presence of inert diluents, such as, for example, toluene, at temperatures between −10° C. and +50° C. in approximately molar amounts (cf. also execution Examples II-1 to II-8).

The starting compounds of the formula (VII) are generally known compounds of organic chemistry.

Examples of compounds of the formula (VII) which may be mentioned are: O-methyl, O-ethyl, O-n-propyl, O-i-propyl, O-n-butyl, O-i-butyl, O-sec.-butyl and O-tert.-butyl (thiono)-phosphate dichloride or dibromide.

The starting compounds of the formula (VIII) are generally known compounds of organic chemistry.

Examples of compounds of the formula (VIII) which may be mentioned are: trifluoromethanol, difluoromethanol 2,2,2-trifluoroethanol, 3,3,3-trifluoropropanol, 2,2,3,3-tetrafluoropropanol, 1,1,1,3,3,3-hexafluoropropan-2-ol, 3,3,3-trifluoro-propan-2-ol and 2,2,3,4,4,4-hexafluorobutan-1-ol.

Examples of halides of the formula (II) which may be mentioned are: O-methyl O-trifluoromethyl, O-ethyl O-trifluoromethyl, O-n-propyl O-trifluoromethyl, O-i-propyl O-trifluoromethyl, O-n-butyl O-trifluoromethyl, O-i-butyl O-trifluoromethyl, O-sec.-butyl O-trifluoromethyl, O-tert.-butyl O-trifluoromethyl, O-methyl O-difluoromethyl, O-ethyl O-difluoromethyl, O-n-propyl O-difluoromethyl, O-i-propyl O-difluoromethyl, O-n-butyl O-difluoromethyl, O-i-butyl O-difluoromethyl, O-sec.-butyl O-difluoromethyl, O-tert.-butyl O-difluoromethyl, O-methyl O-(2,2,2-trifluoroethyl), O-ethyl O-(2,2,2-trifluoroethyl), O-n-propyl O-(2,2,2-trifluoroethyl), O-i-propyl O-(2,2,2-trifluoroethyl), O-n-butyl O-(2,2,2-trifluoroethyl), O-i-butyl O-(2,2,2-trifluoroethyl), O-sec.-butyl O-(2,2,2-trifluoroethyl), O-tert.-butyl O-(2,2,2-trifluoroethyl), O-methyl O-(3,3,3-trifluoropropyl), O-ethyl O-(3,3,3-trifluoropropyl), O-n-propyl O-(3,3,3-trifluoropropyl), O-i-propyl O-(3,3,3-trifluoropropyl), O-n-butyl O-(3,3,3-trifluoropropyl), O-i-butyl O-(3,3,3-trifluoropropyl), O-sec.-butyl O-(3,3,3-trifluoropropyl), O-methyl O-(2,2,3,3-tetrafluoropropyl), O-ethyl O-(2,2,3,3-tetrafluoropropyl), O-n-propyl O-(2,2,3,3-tetrafluoropropyl), O-i-propyl O-(2,2,3,3-tetrafluoropropyl), O-n-butyl O-(2,2,3,3-tetrafluoropropyl), O-i-butyl O-(2,2,3,3-tetrafluoropropyl), O-sec.-butyl O-(2,2,3,3-tetrafluoropropyl), O-methyl O-(1,1,1,3,3,3-hexafluoro-2-propyl), O-ethyl O-(1,1,1,3,3,3-hexafluoro-2-propyl), O-n-propyl O-(1,1,1,3,3,3-hexafluoro-2-propyl), O-n-butyl O-(1,1,1,3,3,3-hexafluoro-2-propyl), O-methyl O-(3,3,3-trifluoro-2-propyl), O-ethyl O-(3,3,3-trifluoro-2-propyl), O-n-propyl O-(3,3,3-trifluoro-2-propyl), O-i-propyl O-(3,3,3-trifluoro-2-propyl), O-n-butyl O-(b 3,3,3-trifluoro-2-propyl), O-methyl O-(2,2,3,4,4,4-hexafluoro-1-butyl), O-ethyl O-(2,2,3,4,4,4-hexafluoro-1-butyl), O-n-propyl O-(2,2,3,4,4,4-hexafluoro-1-butyl), O-i-propyl O-(2,2,3,4,4,4-hexafluoro-1-butyl), O-n-butyl O-(2,2,3,4,4,4-hexafluoro-1-butyl), O-i-butyl O-(2,2,3,4,4,4-hexafluoro-1-butyl), O-sec.-butyl O-(2,2,3,4,4,4-hexafluoro-1-butyl) and O-tert.-butyl O-(2,2,3,4,4,4-hexafluoro-1-butyl) (thiono)-phosphate chloride or bromide.

The 1,6-dihydro-4-hydroxy-6-oxo-pyrimidines of the formula (III) which are furthermore to be used as starting materials for the process version (a) are known and/or can be prepared by generally known processes and methods (cf., for example, DE-OS (German Published Specification) No. 2,630,054 or U.S. Pat. No. 4,152,426).

Examples of compounds of the formula (III) which may be mentioned are:

TABLE 1

| $R^2$ | $R^3$ | $R^4$ |
|---|---|---|
| —$C_2H_5$ | —$C_2H_5$ | H |
| —$C_3H_7$—i | —$CH_3$ | —$C_2H_5$ |
| —$CH_2SCH_3$ | —$CH_3$ | H |
|  | —$CH_3$ | H |
| —$N(CH_3)_2$ | —$CH_3$ | H |
| —$C_3H_7$—i | —$CH_3$ | Cl |
| —$CH_3$ | —$CH_3$ | —$CH_3$ |
| —$CH_3$ | —$C_3H_7$—i | —$C_2H_5$ |
| —$C_3H_7$—n | —$CH_3$ | H |
| —$C_3H_7$—i | —$CH_3$ | H |
| —$SCH_3$ | —$CH_3$ | H |
| —$C_3H_7$—i | 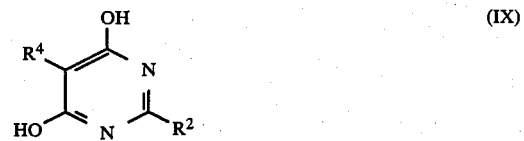 | H |
| —$OCH_3$ | —$CH_3$ | H |
| H | —$C_3H_7$—i | H |
| —$C_3H_7$—i | —$CH_3$ | Br |
| —$CH_3$ | —$C_2H_5$ | —$CH_3$ |
| —$C_4H_9$—t | —$CH_3$ | H |

The O-(6-hydroxy-pyrimidin-4-yl) (thiono)-phosphates of the formula (IV) which are to be used as starting materials for the process version (b) are new and can be prepared by generally conventional processes, by reacting 4,6-dihydroxypyrimidines of the formula (IX)

$$\text{(IX)}$$

in which

R² and R⁴ have the abovementioned meanings, with approximately molar amounts of halides of the formula (II), if appropriate in the presence of acid acceptors, such as, for example, triethylamine, and if appropriate in the presence of diluents, such as, for example, methylene chloride, at temperatures between 0° C. and 60° C.

The same preferred definitions of the radicals as are stated for the formula (I) are valid for the definitions in the formulae (IV) and (IX).

The compounds of the formula (IX) are known compounds of organic chemistry.

Examples of compounds of the formula (IV) which may be mentioned are:

TABLE 2

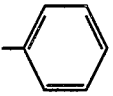

| X | R | R¹ | R² | R⁴ |
|---|---|---|---|---|
| S | —C₂H₅ | —CH₂CF₃ | —CH₃ | H |
| S | —C₂H₅ | —CH₂CF₃ | —C₂H₅ | H |
| S | —C₂H₅ | —CH₂CF₃ | —C₃H₇—i | H |
| S | —C₂H₅ | —CH₂CF₂CHF₂ | —C₃H₇—i | H |
| S | —C₂H₅ | —CH₂CF₂CHF₂ | —C₂H₅ | H |
| S | —C₃H₇—i | —CH₂CF₂CHF₂ | —C₂H₅ | H |
| S | —C₂H₅ | —CH₂CF₃ | —SCH₃ | H |
| S | —C₂H₅ | —CH₂CF₃ | —CH₂SCH₃ | H |
| S | —C₂H₅ | —CH₂CF₃ | —C₃H₇—i | —C₂H₅ |
| S | —C₂H₅ | —CH₂CF₃ | —C₆H₅ (phenyl) | H |
| S | —C₂H₅ | —CH₂CF₃ | —OCH₃ | H |
| S | —C₂H₅ | —CH₂CF₂CHF₂ | —N(CH₃)₂ | H |
| S | —C₂H₅ | —CH₂CF₃ | H | H |
| S | —C₂H₅ | —CH₂CF₃ | —C₃H₇—i | Cl |
| S | —C₂H₅ | —CH₂CF₃ | —C₃H₇—i | Br |
| S | —C₂H₅ | —CH₂CF₂CHF₂ | —C₃H₇—i | Cl |
| S | —C₂H₅ | —CH₂CF₂CHF₂ | —C₃H₇—i | Br |
| S | —CH₃ | —CH₂CF₃ | —C₃H₇—i | H |
| S | —C₃H₇—n | —CH₂CF₃ | —C₂H₅ | H |
| S | —C₂H₅ | —CH(CF₃)₂ | —C₃H₇—i | H |
| S | —C₂H₅ | —CH(CF₃)₂ | —C₂H₅ | H |
| O | —C₂H₅ | —CH₂CF₃ | —C₃H₇—i | H |
| S | —CH₃ | —CH₂CF₃ | —C₄H₉—t. | H |
| S | —CH₃ | —CH₂CF₂CHF₂ | —C₃H₇—i | H |
| S | —C₃H₇—i | —CH₂CF₃ | —C₃H₇—i | H |
| S | —C₃H₇—i | —CH₂CF₂CHF₂ | —C₃H₇—i | H |
| S | —C₃H₇—i | —CH₂CF₃ | —C₄H₉—t | H |

The alkyl halides or dialkyl sulphates which are furthermore to be used for the process versions (b/α) or (b/β) are generally defined by the formula (V) or (VI). In this formula, R³ preferably represents alkyl having 1 to 6 carbon atoms, particularly methyl, ethyl, n-propyl, i-propyl, n-butyl, i-butyl, sec.-butyl and tert.-butyl. In the alkyl sulphates of the formula (VI), R³ preferably represents methyl or ethyl.

Examples of compounds of the formula (V) which may be mentioned are: methyl, ethyl, n-propyl, i-propyl, n-butyl, i-butyl, sec.-butyl and tert.-butyl chloride, bromide or iodide.

Examples of the compounds of the formula (VI) which may be mentioned are: dimethyl, diethyl and di-n-propyl sulphate.

The compounds of the formula (V) and (VI) are known compounds of organic chemistry.

The process versions (a) and (b) according to the invention for the preparation of new compounds of the formula (I) are preferably carried out using diluents. Virtually all inert solvents are suitable as diluents.

These preferably include aliphatic and aromatic, optionally halogenated hydrocarbons such as pentane, hexane, heptane, cyclohexane, pentroleum ether, benzine, ligroin, benzene, toluene, xylene, methylene chloride, ethylene chloride, chloroform, carbon tetrachloride, chlorobenzene and o-di-chlorobenzene, ethers, such as diethyl and dibutyl ether, glycol dimethyl ether and diglycol dimethyl ether, tetrahydrofuran and dioxne, ketones, such as acetone, methyl ethyl, methyl isopropyl and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylenesulphone and hexamethylphosphoric triamide.

The process versions (a) and (b) according to the invention can, if appropriate, be carried out in the presence of acid acceptors. All conventional acid binders can be used as acid acceptors. Alkali metal carbonates, such as sodium and potassium carbonate, alkaline earth metal oxides and hydroxides, such as magnesium oxide and calcium hydroxide, alkali metal hydrides, such as sodium hydride, furthermore aliphatic, aromatic or heterocyclic amines, for example triethylamine, trimethylamine, dimethylaniline, dimethylbenzylamine and piperidine, have particularly proved themselves.

The process versions (a) and (b) according to the invention are, in general, carried out at temperatures between 0° C. and 100° C. The range between 10° C. and 80° C. is preferred. The reaction are, in general, carried out at atmospheric pressure.

To carry out the process version (a), the starting materials are preferably employed in an equimolar ratio. An excess of one or other component brings no significant advantages. The co-reactants are, in general, combined in the stated solvent and stirred for one or more hours until the reaction is complete, usually at elevated temperature. An organic solvent, for example toluene, is then added to the reaction mixture and the organic phase is worked up by conventional methods, by washing, drying and removal of the solvent by distillation.

In process version (b), the alkyl halide of the formula (V) or the dialkyl sulphate of the formula (VI) are employed in equimolar amounts or in 10 to 15% excess, the reaction is carried out, and the products are worked up as described for version (a).

The new compounds are frequently produced in the form of oils which cannot usually be distilled without decomposition, but which can be freed of the final volatile components, in order to be purified in this fashion, by so-called "insipient distillation", that is to say by relatively long heating under reduced pressure at slightly elevated temperatures. They are characterized by the refractive index.

The active compounds are suitable for combating animal pests, in particular insects and arachnida, which are encountered in agriculture, in forestry, in the protection of stored products and of materials, and in the field of hygiene, and have good plant tolerance and favourable toxicity to warm-blooded animals. They are active against normally sensitive and resistant species and against all or some stages of development. The above-mentioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and *Scutigera* spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis*, *Periplaneta americana*, *Leucophanea maderae*, *Blattella germanica*, *Acheta domesticus*, *Gryllotalpa* spp., *Locusta*

*migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodinius prolixus* and Triatoma spp. From the order of the Homoptera, for example, *Aleurodes brassicae, Bemisia tabaci, Trialeurodes, vaporariorum, Aphis gossypii, Brivicoryne brassicae, Cryptomyzus ribis, Aphis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepiodptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Caocecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthomomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, melolontha, Amphimallon solstitialis* and *Costelytra zealandica.* From the order of the Hymenoptera, for example, Diprion spp., Hoplocampa spp., Lasius spp., *Monomorium pharanis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Hyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

In addition, the active compounds according to the invention display a strong microbicidal, especially fungicidal, activity and can be used in plant protection, in particular for combating undesired microorganisms, preferably fungi, which occur on or in plants, and on or in the soil.

Fungicidal agents in plant protection are employed for combating Plamodiophoromycetes, Oomycetes, Cbhytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Phythium species, such as, for example, *Phythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podophaera species, such as, for example, *Podosphaera leucotricha;* Venturia species, such as, for example, *Venturia inaequalis;* Pyrenophora species, such as, for example, *Pyrenophora teres* or *P. graminae (conidia form: Drechslera, syn: Helminthosporium);* Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, or example, Botrytis cinerea; Septoria species, such as, for example, *Septoria nodorum;* Leptosphaeria species, such as, for example, *Leptosphaeria nodorum;* Cercospora species, such as, for example, *Cerocospora canescens;* Alternaria species, such as, for example, *Alternaria brassicae* and Pseudocercosporella species, such as, for example, *Pseudocercosporella hepotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as UVL cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis is products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used hygiene pests and pests of stored products, the active compounds are distinguished by an excellent residual action on wood and clay as well as a good stability to alkali on limed substrates.

The active compounds, according to the invention, of the formula (I) are distinguished by an excellent insecticidal and fungicidal activity. They display an excellent action against grubs such as, for example, *Phorbia antigua* grubs, particularly when used as a soil insecticide, and as fungicides for combating cereal diseases such as, for example, cereal mildew (*Erysiphe graminis*) and true mildew.

The compounds according to the invention can also be employed as leaf insecticides, acaricides and against hygiene and stored product pests.

The effectiveness of the compounds according to the invention will be described by means of the following examples:

The following compounds were employed as comparison substances in the following application examples:

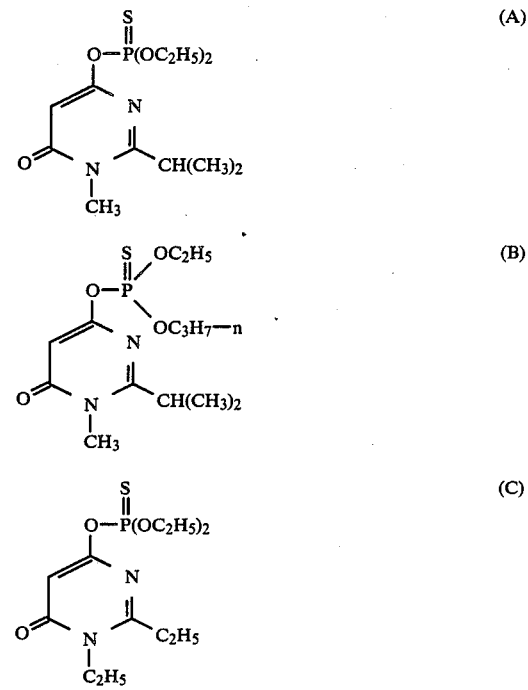

(known from DE-OS (German Published Specification) No. 2,630,054, corresponding to U.S. Pat. No. 4,152,426).

EXAMPLE A

Test insect: Phorbia antiqua maggots (in the soil)
Solvent: 3 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of the preparation Examples 1, 2, 3 and 4, for example, displayed a 100% action at an exemplary concentration of active compound of 10 ppm.

EXAMPLE B

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test using an exemplary concentration of active compound of 0.00025%, the compound from Example 2, for example, displayed a disease infestation of 18.7% and the compound from Example 7 displayed a disease infestation of 45.0%, whereas the comparison compound (C) gave rise to a disease infestation of 100% (in each case relative to the untreated control) at the same concentration.

The preparation of the compounds according to the invention will be described by the following examples:

PREPARATION EXAMPLES

Example 1

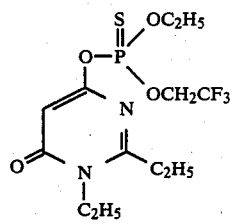

(Process version (a))

A mixture of 8.4 g (0.05 mol) of 1,6-dihydro-1,2-diethyl-4-hydroxy-6-oxo-pyrimidine (preparation cf. U.S. Pat. No. 4,152,426), 10.4 g (0.075 mol) of potassium carbonate, 12.1 g (0.05 mol) of O-ethyl O-(2,2,2-trifluoroethyl)thionophosphate chloride and 200 ml of acetonitrile is stirred for 18 hours at 25° C. After addition of 250 ml of toluene, the mixture is extracted twice with 150 ml of water in each case, the organic phase is dried over sodium sulphate, and the solvent is removed by distillation in vacuo. The residue is insipiently distilled in a high vacuum at 60° C.

9.3 g (49% of theory) of O-ethyl O-(2,2,2-trifluoroethyl) O-(1,2-diethyl-1,6-dihydro-6-oxo-pyrimidin-4-yl) thionophosphate are obtained in this fashion in the form of a beige oil having a refractive index $n_D{}^{22}$: 1.4888.

Example 2

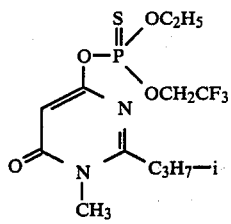

(Process version (b))

31 g (0.08 mol) of O-ethyl O-(2,2,2-trifluoroethyl) O-(6-hydroxy-2-i-propyl-pyrimidin-4-yl) thionophosphate are initially introduced into 60 ml of toluene and treated with 3.5 g (0.047 mol) of calcium hydroxide at 20° to 25° C. 12 g (0.054 mol) of dimethyl sulphate are added dropwise to this mixture at 0° C. to 10° C., and the mixture is stirred for a further 16 hours at 20° C. to 25° C. The reaction mixture is then filtered under suction. The filtrate is washed once with 50 ml of 5% strength sodium hydroxide solution, once with 50 ml of 5% strength hydrochloric acid and twice with 50 ml of water in each case, and is subsequently freed of solvent at 60° C. in vacuo.

26.7 g (83% of theory) of O-ethyl O-(2,2,2-trifluoroethyl) O-(1,6-dihydro-1-methyl-2-i-propyl-6-oxopyrimidin-4-yl) thionophosphate are thus obtained in the form of a yellow oil having the refractive index $n^{22}$: 1.4891.

The following compounds of the formula (I)

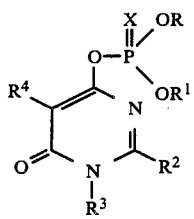

(I)

phosphate are obtained in the form of colorless crystals having the melting point 55° C.

The following, for example, are obtained analogously:

Example (IV-2)

can be prepared, for example, analogously to Example 1 or 2 or by one of processes (a) or (b):

TABLE 3

| Ex. No. | R | $R^1$ | $R^2$ | $R^3$ | $R^4$ | X | Refractive index; melt. pt. [°C.] |
|---|---|---|---|---|---|---|---|
| 3 | $-C_2H_5$ | $-CH_2CF_2CHF_2$ | $-C_3H_7-i$ | $-CH_3$ | H | S | $n_D^{21}$:1.4866 |
| 4 | $-C_2H_5$ | $-CH_2CF_2CHF_2$ | $-C_2H_5$ | $-C_2H_5$ | H | S | $n_D^{22}$:1.4744 |
| 5 | $-C_3H_7-i$ | $-CH_2CF_2CHF_2$ | $-C_2H_5$ | $-C_2H_5$ | H | S | $n_D^{22}$:1.4841 |
| 6 | $-C_2H_5$ | $-CH_2CF_3$ | $-C_3H_7-i$ | phenyl | H | S | 82–84 |
| 7 | $-C_2H_5$ | $-CH_2CF_3$ | $-SCH_3$ | $-CH_3$ | H | S | 50–52 |
| 8 | $-C_2H_5$ | $-CH_2CF_3$ | $-CH_2-S-CH_3$ | $-CH_3$ | H | S | $n_D^{23}$:1.5272 |
| 9 | $-C_2H_5$ | $-CH_2CF_3$ | $-C_3H_7-i$ | $-CH_3$ | $-C_2H_5$ | S | $n_D^{23}$:1.4837 |
| 10 | $-C_2H_5$ | $-CH_2CF_3$ | phenyl | $-CH_3$ | H | S |  |
| 11 | $-C_2H_5$ | $-CH_2CF_3$ | $-OCH_3$ | $-CH_3$ | H | S |  |
| 12 | $-C_2H_5$ | $-CH_2CF_3$ | $-C_4H_9-t.$ | $-CH_3$ | H | S |  |
| 13 | $-C_2H_5$ | $-CH_2CF_3$ | $-C_3H_7-i$ | $-CH_3$ | H | O |  |
| 14 | $-C_2H_5$ | $-CH_2CF_2CHF_2$ | $-N(CH_3)_2$ | $-CH_3$ | H | S |  |
| 15 | $-C_2H_5$ | $-CH_2CF_3$ | H | $-C_3H_7-i$ | H | S |  |
| 16 | $-C_2H_5$ | $-CH_2CF_3$ | $-C_3H_7-i$ | $-CH_3$ | Cl | S |  |
| 17 | $-C_2H_5$ | $-CH_2CF_2CHF_2$ | $-C_3H_7-i$ | $-CH_3$ | Br | S |  |
| 18 | $-CH_3$ | $-CH_2CF_3$ | $-C_3H_7-i$ | $-CH_3$ | H | S |  |
| 19 | $-C_3H_7-n$ | $-CH_2CF_3$ | $-C_2H_5$ | $-C_2H_5$ | H | S |  |
| 20 | $-C_2H_5$ | $-CH(CF_3)_2$ | $-C_3H_7-i$ | $-CH_3$ | H | S |  |

STARTING MATERIALS OF THE FORMULA (IV)

Example (IV-1)

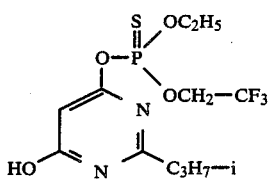

A mixture of 12.9 g (0.084 mol) of 2-isopropyl-4,6-dihydroxy-pyrimidine, 8.8 g (0.0875 mol) of triethylamine and 70 ml of methylene chloride is stirred for one hour at 20° C. and then treated with 17 g (0.07 mol) of O-ethyl O-(2,2,2-trifluoroethyl) thionophosphate chloride at 5° to 10° C. The reaction mixture is stirred for 18 hours at room temperature and then evaporated in vacuo. The residue is treated with 200 ml of toluene and extracted twice with 100 ml of water in each case. The organic phase is dried over sodium sulphate and evaporated in vacuo.

15.2 g (60% of theory) of O-ethyl O-(2,2,2-trifluoroethyl) O-(6-hydroxy-2-i-propyl-pyrimidin-4-yl) thionophosphate

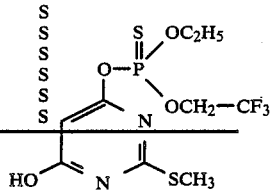

M.p.: 92° C.

Example (IV-3)

$n_D^{22}$: 1.5386.

Example (IV-4)

$n_D^{21}$: 1.4917.

STARTING MATERIALS OF THE FORMULA (II)

Example (II-1)

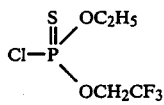

A mixture of 60.5 g (0.5 mol) of collidine and 50 g (0.5 mol) of 2,2,2-trifluoroethanol is added dropwise at 15°–20° C. with slight cooling to a solution of 89.5 g (0.5 mol) of O-ethyl thionophosphate dichloride in 300 ml of toluene. The reaction mixture is stirred for a further 24 hours at 20° C., washed with 100 ml of water, then with 100 ml of 2 percent strength hydrochloric acid and three times with 100 ml of water in each case, and dried over sodium sulphate, and the solvent is evaporated in vacuo.

75.8 g (62% of theory) of O-ethyl O-(2,2,2-trifluoroethyl) thionophosphate chloride are obtained in the form of a colorless oil having the boiling point 62°–64° C./11 mbar.

The following compounds of the formula (II)

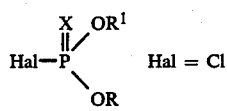         (II)

can be prepared analogously to Example (II-1):

| Ex. No. | R | $R^1$ | X | Physical constants |
|---|---|---|---|---|
| II-2 | $C_2H_5$ | $CHF_2-CF_2-CH_2-$ | S | Bp: 46–49° C./ 0.01 mbar |
| II-3 | $i-C_3H_7$ | $CF_3-CH_2-$ | S | Bp: 68° C./ 14 mbar |
| II-4 | $CH_3$ | $CF_3-CH_2-$ | S | |
| II-5 | $C_2H_5$ | $CF_3-CH_2-$ | O | |
| II-6 | $C_2H_5$ | $(CF_3)_2CH-$ | S | |
| II-7 | $n-C_3H_7$ | $CF_3-CH_2-$ | S | |
| II-8 | $i-C_3H_7$ | $CHF_2-CF_2-CH_2-$ | S | $n_D^{21}$: 1.4486 |

It will be understood that the specification and examples are illustrative but not limitative of the present invention and that other embodiments within the spirit and scope of the invention will suggest themselves to those skilled in the art.

We claim:

1. A 6-oxo-pyrimidinyl(thiono)-phosphate of the formula

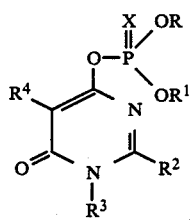

in which

X represents oxygen or sulphur,

R represents alkyl having 1 to 6 carbon atoms, $R^1$ represents fluoroalkyl having 1 to 6 carbon atoms and 1 to 6 fluorine atoms, $R^2$ represents hydrogen, alkyl, having 1 to 6 carbon atoms, which is optionally substituted by fluorine, chlorine, bromine, nitro, cyano, $C_1$–$C_4$-alkoxy or $C_1$–$C_4$-alkylthio, alkoxy, alkylthio or dialkylamino having 1 to 6 carbon atoms in each of the alkyl parts, or phenyl, $R^3$ represents alkyl having 1 to 6 carbon atoms, or phenyl and $R^4$ represents hydrogen, fluorine, chlorine, bromine, or alkyl having 1 to 6 carbon atoms.

2. A compound according to claim 1, in which

R represents alkyl having 1 to 4 carbon atoms, $R^1$ represents fluoroalkyl having 1 to 4 carbon atoms and 1 to 6 fluorine atoms, $R^2$ represents hydrogen, alkyl, having 1 to 4 carbon atoms, which is optionally substituted by fluorine, chlorine, methoxy, ethoxy, methylthio or ethylthio, alkoxy having 1 to 4 carbon atoms, alkylthio having 1 to 4 carbon atoms, dialkylamino having 1 to 4 carbon atoms per alkyl radical, or phenyl, $R^3$ represents alkyl having 1 to 4 carbon atoms, or phenyl and $R^4$ represents hydrogen, fluorine, chlorine, bromine or alkyl having 1 to 4 carbon atoms.

3. A compound according to claim 1, wherein such compound is O-ethyl O-(2,2,2-trifluoroethyl) O-(1,2-diethyl-1,6-dihydro-6-oxo-pyrimidin-4-yl) thionophosphate of the formula

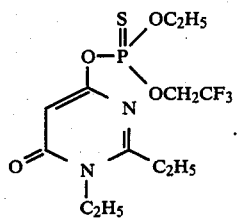

4. A compound according to claim 1, wherein such compound is O-ethyl O-(2,2,2-trifluoroethyl) O-(1,6-dihydro-1-methyl-2-i-propyl-6-oxo-pyrimidin-4-yl) thionophosphate of the formula

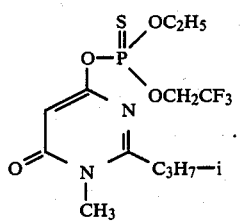

5. A compound according to claim 1, wherein such compound is O-ethyl O-(2,2,3,3-tetrafluoropropyl) O-(1-methyl-2-isopropyl-1,6-dihydro-6-oxo-pyrimidin-4-yl) thionophosphate of the formula

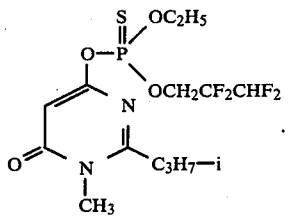

6. A compound according to claim 1, wherein such compound is O-ethyl O-(2,2,3,3-tetrafluoropropyl) O-(1,2-diethyl-1,6-dihydro-6-oxo-pyrimidin-4-yl) thionophosphate of the formula

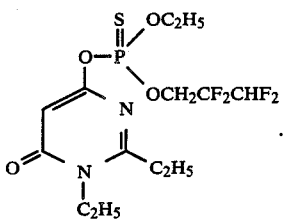

7. A compound according to claim 1, wherein such compound is O-ethyl O-(2,2,2-trifluoroethyl) O-(1-methyl-2-methylthio-1,6-dihydro-6-oxo-pyrimidin-4-yl) thionophosphate of the formula

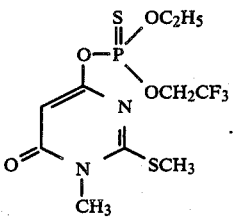

8. An insecticidal or fungicidal composition comprising an insecticidally or fungicidally effective amount of a compound according to claim 1 and a diluent.

9. A method of combating insects or fungi which comprises applying to such insects or fungi or to an insect or fungus habitat an insecticidally or fungicidally effective amount of a compound according to claim 1 and a diluent.

10. The method according to claim 9, wherein such compound is
O-ethyl)-(2,2,2-trifluoroethyl) O-(1,2-diethyl-1,6-dihydro-6-oxo-pyrimidin-4-yl) thionophosphate,
O-ethyl O-(2,2,2-trifluoroethyl) O-(1,6-dihydro-1-methyl-2-i-propyl-6-oxo-pyrimidin-4-yl) thionophosphate,
O-ethyl O-(2,2,3,3-tetrafluoropropyl) O-(1-methyl-2-isopropyl-1,6-dihydro-6-oxo-pyrimidin-4-yl) thionophosphate,
O-ethyl O-(2,2,3,3-tetrafluoropropyl) O-(1,2-diethyl-1,6-dihydro-6-oxo-pyrimidin-4-yl) thionophosphate or
O-ethyl O-(2,2,2-trifluoroethyl) O-(1-methyl-2-methylthio-1,6-dihydro-6-oxo-pyrimidin-4-yl) thionophosphate.

11. An O-(6-hydroxypyrimidin-4-yl) (thiono)-phosphoric acid ester of the formula

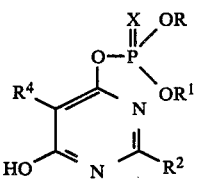

in which
X represents oxygen or sulphur,
R represents alkyl,
$R^1$ represents fluoroalkyl,
$R^2$ represents hydrogen, optionally substituted alkyl, or alkoxy, alkylthio, dialkylamino or aryl, and
$R^4$ represents hydrogen, halogen or alkyl.

* * * * *